United States Patent [19]

Dörre et al.

[11] 4,312,079
[45] Jan. 26, 1982

[54] FEMUR HEAD CAP FOR ENDOPROSTHESIS

[75] Inventors: Erhard Dörre, Plochingen; Peter Prüssner, Dietzenbach; Ludwig Zichner, Neu-Isenburg-Grafenbruch, all of Fed. Rep. of Germany

[73] Assignee: Feldmühle Aktiengesellschaft, Duesseldorf, Fed. Rep. of Germany

[21] Appl. No.: 136,087

[22] Filed: Mar. 31, 1980

[30] Foreign Application Priority Data

Apr. 11, 1979 [DE] Fed. Rep. of Germany ....... 2914737

[51] Int. Cl.³ .............................................. A61F 1/03
[52] U.S. Cl. ................................ 3/1.913; 128/92 CA; 128/92 E
[58] Field of Search ...................... 3/1.9, 1.912, 1.913; 128/92 CA

[56] References Cited

U.S. PATENT DOCUMENTS

| 3,925,824 | 12/1975 | Freeman et al. | 128/92 CA X |
| 4,005,495 | 2/1977 | Locke et al. | 3/1.913 X |
| 4,073,999 | 2/1978 | Bryan et al. | 3/1.9 X |
| 4,224,699 | 9/1980 | Weber | 3/1.913 |

FOREIGN PATENT DOCUMENTS

| 923383 | 2/1955 | Fed. Rep. of Germany | 128/92 CA |
| 2845231 | 5/1979 | Fed. Rep. of Germany | 3/1.912 |
| 720092 | 12/1954 | United Kingdom | 128/92 CA |
| 759908 | 10/1956 | United Kingdom | 128/92 CA |
| 619179 | 8/1978 | U.S.S.R. | 128/92 CA |

Primary Examiner—Clifford D. Crowder
Attorney, Agent, or Firm—Toren, McGeady and Stanger

[57] ABSTRACT

A femur head cap for endoprosthesis possessing a spherical shape and having a recess for partially receiving the femur head, the recess being open toward the neck of the femur. The cap is advantageous in that it can be firmly anchored to avoid rotation and tilting without the use of bone cement and further allows for simple resection to be performed so that supply of blood to the bone is not impaired.

11 Claims, 9 Drawing Figures

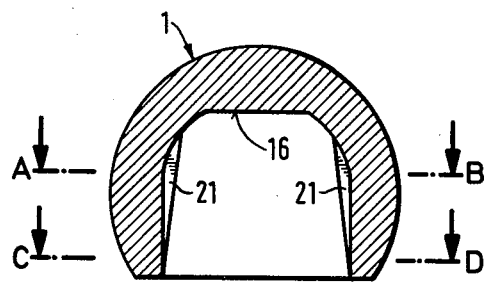
Fig. 6 (E-F)
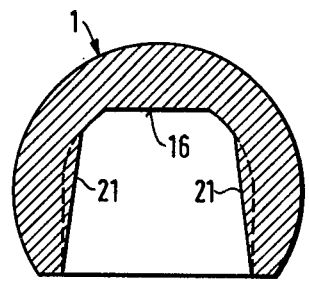
Fig. 8 (G-H)
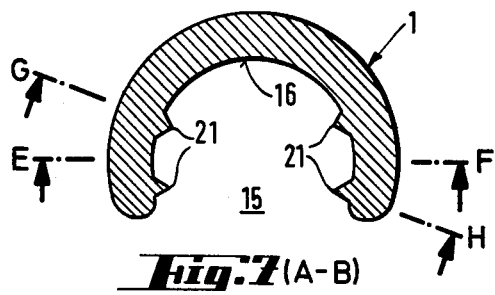
Fig. 7 (A-B)
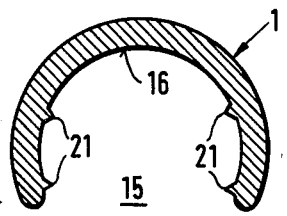
Fig. 9 (C-D)

FEMUR HEAD CAP FOR ENDOPROSTHESIS

BACKGROUND OF THE INVENTION

1. Field of the Invention

The invention relates to a cap for the hip head or femur head for endoprostheses. The cap has an essentially spherical shape and has a recess for partially receiving the femur.

2. Description of the Prior Art

The use of spherical caps at the proximal end of the femur is known and is described, for example, in British Pat. Nos. 720,092, 764,600, U.S. Pat. Nos. 3,521,302, 3,925,824, German Offenlegungsschriften Nos. 27 24 040, 25 12 407, 25 35 649, 24 22 617, and German Pat. Nos. 1,164,019, 923,383.

It is common in this art that for insertion, work must be performed on the entire femur head. In most cases, this work essentially destroys the supply vessels of the neck of the femur, i.e., the blood supply to the bone stump is no longer ensured. This causes necroses of the stump and, as a result, a loosening of the spherical cap.

Another significant difficulty with the previous fastenings of the spherical caps resided in preventing their rotational movement. For example, it has already been suggested to provide vertical ribs or grooves in the spherical cavity, see British Pat. No. 720,092, and U.S. Pat. No. 3,925,824, or to achieve securement through fastening pins which simultaneously are supposed to serve as the primary anchoring, see U.S. Pat. No. 3,521,302, German Pat. No. 1,164,019, and German Pat. No. 923,383.

In other caps, the fastening was effected by means of bone cement. However, the tissue is severely damaged by the heat load occurring during hardening. Also, toxic phenomena caused by the monomer of the bone cement are possible.

SUMMARY OF THE INVENTION

We have discovered a substitute joint surface for the proximal end of the femur which is simple to implant, requires only a minimum resection so that, in the case of failure, all other possible treatments remain available, such as, arthrodesis or conventional total endoprosthesis. The surface of the present invention changes only the tribological, but not the biomechanical conditions, because the neck of the femur is completely preserved. Furthermore, this ensures a satisfactory supply to the vessels, facilitates a rigid primary fixation without bone cement and the growing-in of bone structures for an additional long-term anchoring.

More particularly, the present invention comprises a femur head cap as an endoprosthesis which has an essentially spherical shape and a recess for partially receiving the femur, wherein the recess in the femur head cap is open toward the neck of the femur. When viewed from the side, the femur head cap had the shape of a bathing cap wherein the opening for the face provided in the bathing cap faces toward the neck of the femur. Thus, the important vessels which supply the stump are not damaged. As a result, the supply of the bone is preserved and only a minimum resection is required. This makes it possible to perform a subsequent operation at any time in which, if necessary, conventional prostheses can be implanted.

BRIEF DESCRIPTION OF THE DRAWINGS

FIGS. 6 to 9 show sections taken through the femur head cap.

DESCRIPTION OF THE PREFERRED EMBODIMENT

Figure 1:
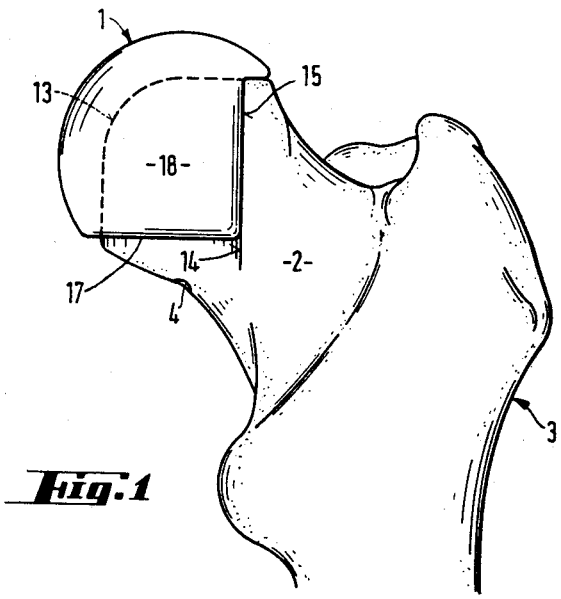
FIG. 1 shows a proximal end of a femur with a femur cap placed thereon.
Figure 2:
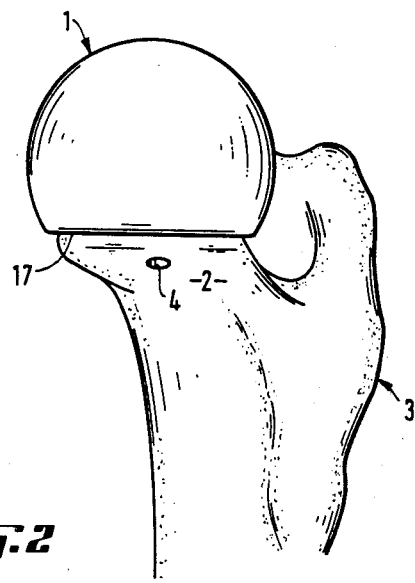
FIG. 2 shows the same proximal end of the femur with the femur cap placed thereon, however, the femur is turned by approximately 45 degrees.

In accordance with a preferred embodiment of the invention and referring to FIGS. 1 to 5, the recess 16 of the femur head cap 1 is partially cylindrical with an opening 15 towards the neck 2 of the femur 3. In another preferred embodiment, the recess can be in the form of an open truncated cone. The opening of the recess 16 preferably has a smaller inner width than the greatest width of the recess itself, e.g., see FIG. 8.

The design of the recess as a cylinder or truncated cone, to wit, as an axially symmetric body, substantially simplifies the work on the end of the femur. By providing a centering bore 4 in the head of the femur, the resection of the head of the femur by means of an oscillating saw is possible. As a result, significantly narrower tolerances can be maintained. Furthermore, the work on the areas of the head of the femur which are located in the rearward operating region becomes simpler.

Due to the fact that the opening of the recess has a smaller inner width than the greatest width of the recess itself, the cylindrical stump is surrounded by the femur head cap by more than 180 degrees, i.e., the femur head cap is securely anchored and cannot tilt. The safety against rotation of the femur head cap is ensured by the stops of the femur head which have not been cut and against which the ends of the openings of the recess are bearing.

In accordance with the preferred embodiment of the invention, the center axis of the recess extends essentially parallel of the center axis of the femur. This arrangement of the femur head cap advantageously influences the introduction of the forces into the substitute joint surface so that the cap can be anchored so as to be absolutely stable with respect to rotation and tilting, without any additional fixing means, i.e., especially without bone cement.

In another preferred embodiment of the invention, the femur head cap is connected to the femur through a force fit. Fastening by means of a force fit also ensures excellent primary fixation without requiring any bone cement. However, an essential prerequisite for the placement of a femur head cap is that narrow tolerances are maintained between the femur head and the recess of the femur head cap. The placement of a femur head cap through a force fit is only possible when an accurate adherence to the tolerances is ensured, i.e., which means that the mechanical work on the femur head for the resection is performed by means of an accurately guided tool. For this purpose, an oscillating concave cutter has been found especially advantageous, wherein, depending on the shape of the concave cutter, the resected parts have a cylindrical or a conical shape while, on the other hand, the resection is performed in such a way that the work on the bone never takes place toward the neck of the femur or the base of the femur head cap. This ensures that the supply of the vessels is not impaired.

The recess of the femur head cap is advantageously provided with grooves 19 and/or ribs 21 which extend parallel and/or perpendicular of the center axis of the cylinder or the cone. These grooves or ribs provide the space required for the secondary anchoring, to wit, the space into which the bone structures can grow and thereby result in a rigid anchoring of the femur head cap. However, because of the occurring loads, it is advisable to arrange these grooves or ribs only in the side portions and not in the frontal portion of the femur head cap, because the greater load occurs in the frontal portion and, therefore, a weakening of the femur head cap in this region must be avoided.

It is particularly advantageous to provide the entire recess with a rough surface. This rough surface can be provided in the femur head cap during the finishing procedure of the recess. However, it is also possible to provide this rough surface by a subsequent application of another layer. For example, the application can be performed by flame or plasma spraying.

The rough surface is particularly important in the region of the sides of the femur head cap, because as is true for the ribs or grooves, it provides a better surface for the bone to grow into. Also, the frontal surface is thereby not weakened. The surface of the recess is advantageously provided with pores whose size is greater than 80 micron since experience has shown, that pores of a size of below 60 micron do not provide a support for the ingrowing bone and pores below 80 micron provide only insignificant fastening. An effective, true fastening occurs preferably with a pore size of greater than about 100 micron.

Practically all biocompatible substances can be used as the material for the femur head cap. However, it must be ensured that the material does not cause abrasion in the cooperation with the socket. For example, combinations of a femur head cap of metal with a socket of polyethylene can be used as can carbon, cobalt base alloys, as well as special steels and titanium. However, due to the extremely low abrasion values which are practically near zero, and the excellent compatibility with the body, oxide ceramics are preferred.

In accordance with a very advantageous embodiment of the present invention, the femur head cap consists of extremely pure, sintered oxide ceramics. The term "extremely pure" means that the sintered oxide ceramics have a purity of higher than 95 percent, and, in the sense of the above explanations, the term "sintered oxide ceramics" is understood to refer to the sintered metal oxides of zirconium, titanium and especially aluminum and mixtures thereof. Preferably, the femur head cap consists of a sintered aluminum oxide with a density equal to or greater than 3.92 g/cm$^3$,
a porosity equal to or less than 2%,
a water absorption equal to or less than 0.01%,
a purity equal to or greater than 99.7% $Al_2O_3$,
a [Vickers]pyramid hardness (P=2 M) equal to or greater than 22,000 N/mm$^2$,
an average grain size equal to or smaller than 10 micron,
an average bending strength equal to or greater than 300 N/mm$^2$,
a compressive strength equal to or greater than 4,000 N/mm$^2$, and
a tensile strength equal to or greater than 160 N/mm$^2$.

Such a material provides the required high safety characteristics for an endoprosthesis which will last for decades, the excellent properties being obtained especially by the combination of the high density with the small average grain size and the high purity of the sintered aluminum oxide. In this connection, purity means that the aluminum oxide contains as few foreign materials as possible as additional components which could lead to a glass-like intermediate or transition phase. However, it is possible to add certain materials, such as, magnesium oxide for retarding the grain growth, to the initial powder, i.e., the aluminum oxide.

For testing the new concept of the femur head caps of the present invention, experiments with animals as well as corpses were performed. After exposing the hip joint, a bore was made parallel of the center axis of the femur through the pole of the femur head. This bore served the purpose of guiding the centering pin of an oscillating concave cutter by means of which the cylindrical bearing for the implant was prepared. Subsequently, at an angle of 90 degrees relative to the center axis of the cylinder, a spherical segment was resected.

The resection was performed in the manner of a counterbore by means of a rotating face milling cutter guided in the bore. The upper edges of the resulting bone cylinder were rounded off with an instrument which was also guided with a centering pin in the bore. Subsequently, the cap was placed with a force fit. The experiment on corpses showed that the femur head cap has significant advantages for the use in human patients, because only a minimum resection was required, and because a good supply of the vessels could be ensured and a rigid primary fixation was achieved without bone cement. After repositioning, the function of the hip joint was checked and no impediments or luxations occurred.

The animal experiment was performed on foxhounds which, fourteen days after the operation, showed decreasing noticeable abnormal walking behavior. They recovered quickly and could be brought back to the kennel two months later and, in the natural sourrounding of the pack, they exhibited great mobility. They were able to fully assert themselves in the pack after the operation which affirmed, as did the x-ray photograph, the complete operativeness and the problem-free healing of the inserted femur head cap of extremely pure aluminum oxide ceramics.

Figure 3:
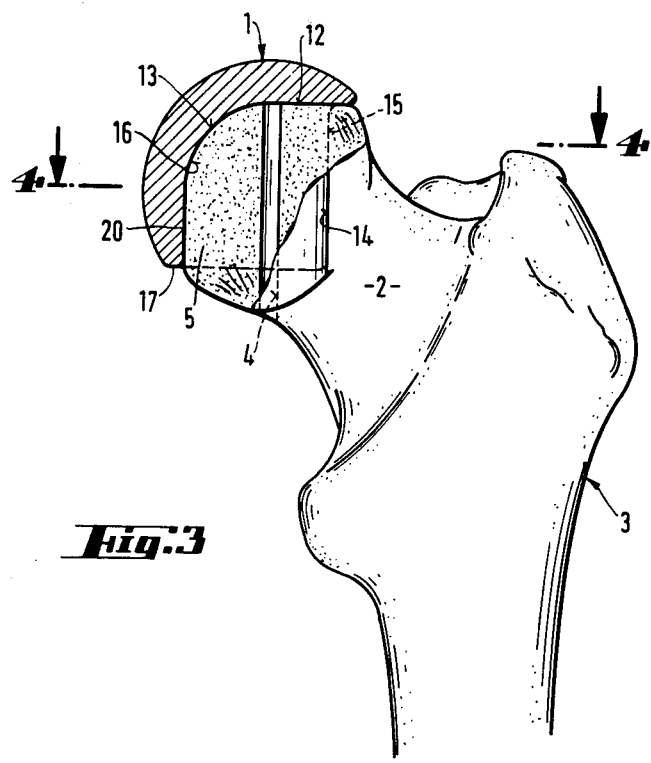
FIG. 3 shows a median section taken through the resected femur head parallel of the axis of the femur, with the femur cap in place.
Figure 4:
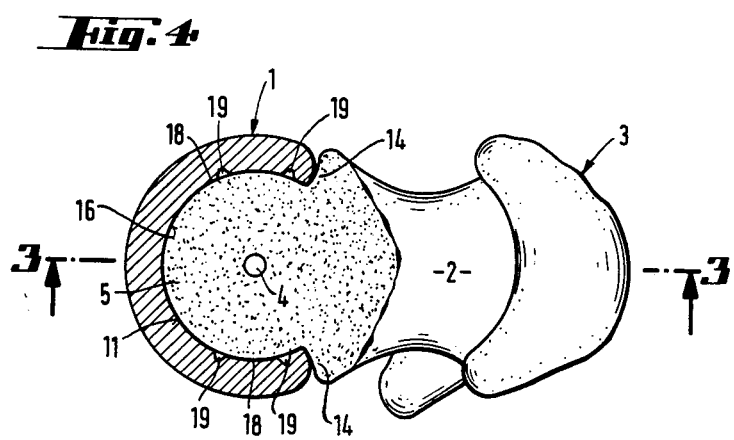
FIG. 4 shows the section taken through the resected femur head at a 90 degree angle relative to the axis of the femur, with the femur cap in place.
Figure 5:
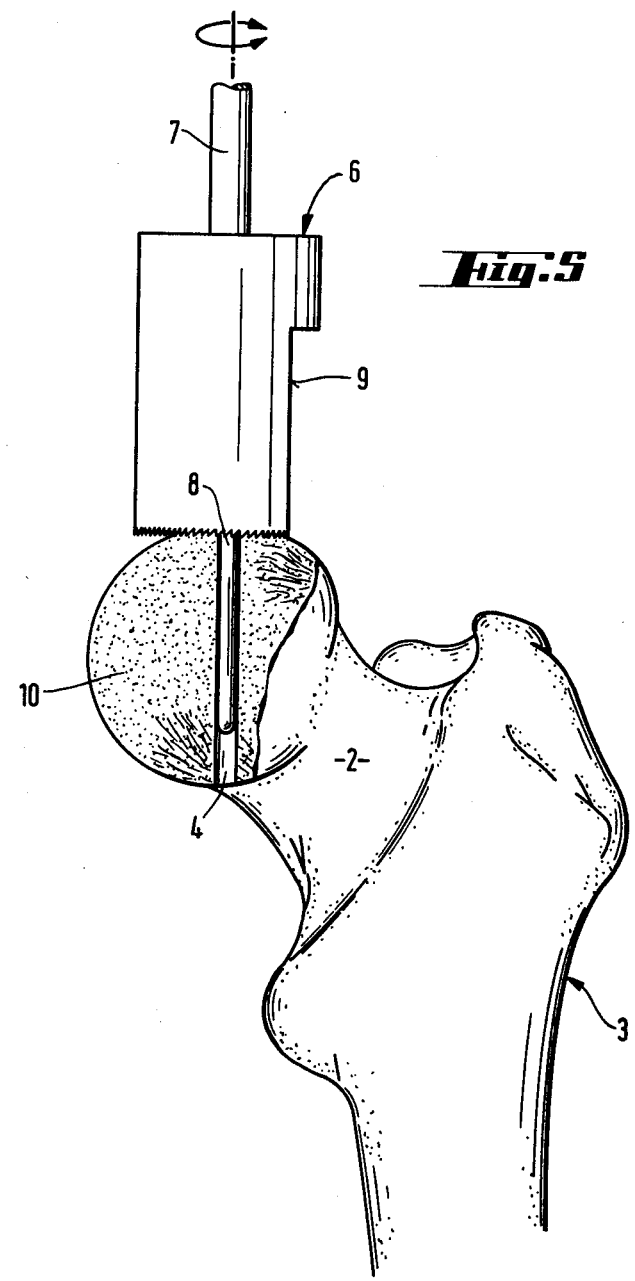
FIG. 5 schematically shows the resection by means of an oscillating concave cutter.

Referring to FIGS. 3, 4 and 5, the resection of the femur head is shown. A bore hole 4 is made in the femure head 10 by means of a drill, not shown. The bore hole 4 serves for guiding the centering pin 8 of the concave cutter 6. The concave cutter 6 has an attachment 7 on which an oscillating saw acts, not shown, which moves the concave cutter 6 along a circular arc 11. Analogously, by means of a face milling cutter, not shown, which is also guided in the bore hole 4 by means of a centering pin 8, the head surface of the femur head 10 is worked off. As is evident from FIGS. 1, 2 3 and 4, the longitudinal center axis of the cylindrical recess is essentially parallel to the longitudinal outer axis of the femur.

The resection of the femur head 10 by means of the concave cutter 6 resulted in stops 14 at the end of the circular arc 11; these stops 14 prevent a rotation of the femur head cap 1. The opening 15 of the recess 16 in the femur head cap 1 is directed toward the neck 2 of the femur 3, i.e., the resected femur head stump 5 has no damaged vessels in the bottom region 17 of the femur head cap 1 as well as in the region of the femur neck 2. To avoid damage of the vessels on the femur neck 2, the concave cutter 6 is provided with a recess 9 and is turned only by a slight oscillating movement in order to form the circular arc 11. After the rounded section 13 has been formed, the femur head cap 1 can be pressed on which thereby receives its final fit. At its side surfaces 18, it has grooves 19 into which the bone material can grow. The end face 20 does not have grooves 19 in order not to reduce the strength of the femur head cap 1.

FIGS. 6 to 9 show sections taken through the femur head cap 1, each of these caps being provided with conically extending ribs 21. The conical ribs 21 have a triangular shape. They can be pressed in by forcing them into the resected femur head stump 5. The primary fastening is increased by these ribs and the femur head cap 1 is thereby even more stably anchored with respect to rotation.

What is claimed is:

1. A femur head cap for an endoprosthesis, having an essentially spherical shape, and a cylindrical recess for partially receiving the femur, said recess being open toward the neck of the femur and the longitudinal axis of the recess extending essentially parallel with the longitudinal center axis of the femur.

2. A femur head cap for an endoprosthesis, having an essentially spherical shape, and a recess for partially receiving the femur, said recess being a truncated cone which is open toward the neck of the femur and the longitudinal axis of the recess extending essentially parallel with the longitudinal center axis of the femur.

3. A femur head cap for an endoprosthesis, having an essentially spherical shape, and a recess for partially receiving the femur, said recess being open toward the neck of the femur and the longitudinal axis of the recess extending essentially parallel with the longitudinal center axis of the femur wherein the opening of the recess has a smaller inner width than said recess.

4. The femur head cap of claim 1, 2 or 3, wherein the cap is connected to the femur head stump by means of a force fit.

5. The femur head cap of claim 1, 2 or 3, wherein the recess is provided with grooves or ribs extending parallel to the center axis of the recess.

6. The femur head cap of claim 1, 2 or 3, wherein the recess is provided with grooves or ribs which contact only the side portion of the femur head.

7. The femur head cap of claim 1, 2 or 3, wherein the recess has a rough surface.

8. The femur head cap of claim 1, 2 or 3, wherein the surface of the recess is provided with pores whose size is greater than 80 micron.

9. The femur head cap of claim 1, 2 or 3, wherein the femur head cap consists of extremely pure oxide ceramics.

10. The femur head cap of claim 1, 2 or 3, consisting of a sintered aluminum oxide with a density equal to or greater than 3.92 g/cm$^3$, a porosity equal to or less than 2%, a water absorption equal to or less than 0.01%, a purity equal to or greater than 99.7% $Al_2O_3$, a Vickers pyramid hardness (P=2 M) equal to or greater than 22,000 N/mm$^2$, an average grain size equal to or smaller than 10 micron, an average bending strength equal to or greater than 300 N/mm$^2$, a compressive strength equal to or greater than 4,000 N/mm$^2$ and a tensile strength of equal to or greater than 160 N/mm$^2$.

11. The femur head cap of claim 1, 2 or 3 wherein the recess is provided with grooves or ribs extending perpendicular to the center of the axis of the recess.

* * * * *